(12) United States Patent
Chapdelaine et al.

(10) Patent No.: US 6,939,896 B2
(45) Date of Patent: Sep. 6, 2005

(54) CD45 INHIBITORS

(75) Inventors: Marc Jerome Chapdelaine, Wilmington, DE (US); Katherine Knappenberger, Wilmington, DE (US); Gary Steelman, Wilmington, DE (US); Suzanne Suchard, Wilmington, DE (US); Linda Sygowski, Wilmington, DE (US); Rebecca Urbanek, Wilmington, DE (US); Chris Allan Veale, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 134 days.

(21) Appl. No.: 10/168,475
(22) PCT Filed: Dec. 18, 2000
(86) PCT No.: PCT/GB00/04872
§ 371 (c)(1), (2), (4) Date: Nov. 13, 2002
(87) PCT Pub. No.: WO01/45681
PCT Pub. Date: Jun. 28, 2001

(65) Prior Publication Data
US 2003/0119897 A1 Jun. 26, 2003

Related U.S. Application Data
(60) Provisional application No. 60/172,786, filed on Dec. 21, 1999.

(51) Int. Cl.[7] .................. A61K 31/22; C07C 50/10; C07C 50/12
(52) U.S. Cl. ..................... 514/682; 552/292
(58) Field of Search .................... 552/292; 514/682

(56) References Cited

U.S. PATENT DOCUMENTS

| | | | | |
|---|---|---|---|---|
| 5,508,310 A | * | 4/1996 | Rhodes ............... | 514/576 |
| 5,684,035 A | * | 11/1997 | Kapadia ............... | 514/429 |
| 5,866,569 A | | 2/1999 | Mjalli et al. | |
| 5,883,270 A | * | 3/1999 | Frydman et al. ......... | 552/292 |

FOREIGN PATENT DOCUMENTS

WO  WO97/31611  * 9/1997

OTHER PUBLICATIONS

Perumal et al., "Oxidation of halophenols and highly substituted phenols with lead(IV) acetate." Synthesis, vol. 1980 (11), pp. 943–945, Nov. 1980.*

Takuwa et al., "The addition of alcohol to 1,2–naphthoquinone promoted by metal ions. A facile synthesis of 4–alkoxy–1,2–naphthoquinones." Bull. of hte Chem. Soc. of Japan, vol. 59, pp. 2959–2961, 1986.*

Itahara, "Oxidative coupling of quinones and aromatic compounds by palladium (II) acetate." J. Org. Chem., vol. 50, pp. 5546–5550, 1985.*

Henrion et al., "Condensation indole/1,2–naphthoquinone. Recherche des conditions optimales dans la preparation d'une nouvelle serie de 4–(3–indolyl)–1,2–naphtoquinones." Bull. des societes chimisques belges, vol. 105(7), pp. 415–418, 1996.*

Grinev et al., "Synthesis of bis(diethylaminoethyl)–1, 2–dimethyl–8–oxoindeno–[2,1–b]pyrrole–3,5–dicarboxylate." Chem. Heterocyclic Compounds (English translation), vol. 19, pp. 876–879, 1983.*

P. Perumal et al.: "Oxidation of Halophenols and Highly Substituted Phenols with Lead (IV) Acetate" SYNTHESIS, vol. 1980, No. 11, Nov. 1980, pp. 943–945, XP001026188 p. 944, compounds 1a and 2a.

A. Takuma et al.: "The Addition of Alcohol to 1,2–Naphthoquinone Promoted by Metal Ions. A Facile Synthesis of 4–Alkoxyl–1, 2–Naphthoquinones" Bulletin of the Chemical Society of Japan, vo. 59, Sep. 1986, pp. 2959–2961, XP002142395 p. 2959, compounds 2a–2f.

T. Itahara: "Oxidative Coupling of Quinones and Aromatic Compounds by Palladium (II) Acetate." Journal of Organic Chemistry, vol. 50, 1985, pp. 5546–5550, XP002044654, p. 4455, Table I, compounds 8a and 8c.

J.C. Henrion et al.: "Condensation Indole–1,2–naphthoquinone. Recherche des Conditions Optimales dans la Preparation d'une Nouvelle Serie de 4—(3–Indolyl)–1, 2–naphthoquinones. " Bulletin Des Societes Chimiques Belges, vol. 105, No. 7, 1996, pp. 415–418, XP001026771 p. 416, compounds 3a–3e.

(Continued)

Primary Examiner—Barbara P. Badio
(74) Attorney, Agent, or Firm—Kenneth F. Mitchell

(57) ABSTRACT

Substituted naphthalenediones in accord with structural diagram (I): compositions thereof and methods for the use thereof, for the treatment of T cell mediated conditions such as autoimmune diseases and organ graft rejection. In compounds of the invention, wherein: $Q^1$ at each occurrence is independently selected from hydrogen, hydroxy, halogen, $C(O)O(C_1–C_3)$ alkyl and $C(O)$phenyl, and $Q^2$ is selected from hydrogen, halogen, $O—(C_1–C_3)$alkyl, $O—(C_1–C_3)$ alkenyl, phenyl, indolyl and naphthyl, where phenyl may be mono- or di-substituted with $NO_2$ or halogen, and indolyl may be substituted with $(C_1–C_3)$alkyl or phenyl

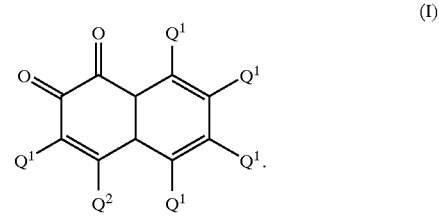

(I)

3 Claims, No Drawings

OTHER PUBLICATIONS

A.N. Grinev et al.: "Synthesis of bis(diethylaminoethyl)–1,2–dimethyl–8–oxoindeno [2,1–b] pyrroloe–3,5–dicarboxylate." Chemistry of Heteroxyxlic Compounds (English Translation), vol. 19, 1983, pp. 876–879, XP001026781 p. 877, compound No. 1.

R.A. Urbanek et al. : "Potent Reversible Inhibitors of the Protein Tyrosine Phosphatase CD45" Journal of Medicinal Chemistry, vol. 44, 2001, pp. 1777–1793, XP001014517 tables 1–3.

* cited by examiner

CD45 INHIBITORS

RELATED APPLICATIONS

This is a 371 of International Application No. PCT/GB00/04872, filed Dec. 18, 2000 which claims priority pursuant to 35 U.S.C. § 119(e) of Provisional Application No. 60/172,786, filed Dec. 21, 1999.

BACKGROUND

1. Field of the Invention

Compounds, compositions and methods for the treatment of immunologically-related diseases and disorders such as autoimmune disorders and organ graft rejection.

2. Related Art

Action of the immune system is known to be involved in immunologically-related diseases and disorders such as autoimmune disorders and in organ graft rejection ("OGR"). Hematopoietic, thymus-derived cells, (so-called "T cells") have an important and pervasive role as regulators and effectors of the functions of the immune system. Hematopoietic cells, and T cells in particular have on their surfaces a major transmembrane glycoprotein designated CD45, characterized by a cluster of antigenic determinants. CD45 is also known as leukocyte common antigen ("LCA"). The cytosolic portion of CD45 has protein tyrosine phosphatase ("PTP") activity and CD45 activity is known to be essential for TCR initiated T cell activation. Studies in CD45-deficient cell lines have shown that CD45 is a positive regulator of the T-Cell Receptor ("TCR") and that CD45 functions in TCR regulation by dephosphorylating the src kinases $p56^{lck}$ and $p59^{fyn}$, which allows autophosphorylation of the positive regulatory site on these enzymes; these reactions lead to downstream events and ultimately to T cell activation.

Available treatments for autoimmune disorders and OGR have therapeutic disadvantages. For example, Cyclosporin A, the drug most commonly used to treat OGR, has renal and CNS toxicity.

SUMMARY OF THE INVENTION

Potent inhibitors of CD45 have been discovered. Such inhibitors are useful for the treatment of various autoimmune disorders as well as for treatment of OGR. Inhibition of the phosphatase activity of CD45 by compounds of the present invention has been shown by incubating the cytosolic portion of CD45 with the compounds and p-nitrophenyl phosphate (pNPP), a phosphatase substrate. Spectrophotometric monitoring has shown that the liberation of p-nitrophenol from the substrate by CD45 is inhibited in the presence of the compounds disclosed herein. Inhibition of the phosphatase activity of CD45 by compounds of the present invention has also been shown using a $p56^{lck}$ carboxy-terminal phosphorylated peptide as a substrate. Compounds of the present invention have also been shown to inhibit proliferation of T cells in a T-cell proliferation assay.

Compounds of the present invention are naphthalenediones in accord with structural diagram I:

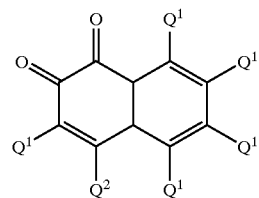

wherein:

$Q^1$ at each occurrence is independently selected from hydrogen, hydroxy, halogen, $C(O)O(C_1-C_3)$alkyl and $C(O)$phenyl, and $Q^2$ is selected from hydrogen, halogen, $O-(C_1-C_3)$alkyl, $O-(C_1-C_3)$alkenyl, phenyl, indolyl and naphthyl, where phenyl may be mono- or di-substituted with $NO_2$ or halogen, and indolyl may be substituted with $(C_1-C_3)$alkyl or phenyl.

Particular compound of the invention are 4-(4-bromo-phenyl)-[1,2]naphthoquinone; 4-(3,5-dichloro-phenyl)-[1,2]naphthoquinone; 4-(3-nitro-phenyl)-[1,2]naphthoquinone; 5,6-dioxo-5,6-dihydro-naphthalene-1-carboxylic acid methyl ester, and 5,6-dioxo-5,6-dihydro-naphthalene-2-carboxylic acid methyl ester.

Compounds of the present invention are ligands of CD45 which, when bound, inhibit the activity of the protein tyrosine phosphatase (PTP) activity of the cytosolic portion of CD45. Binding of a compound of the present invention to CD45 inhibits the activity of CD45 essential for TCR initiated T cell activation. Thus, compounds of the invention inhibit the positive regulation of the TCR that leads to downstream events and T cell activation. Compounds of the present invention are useful to suppress the action of the immune system in immunologically-related diseases and disorders such as autoimmune disorders and organ graft rejection and to inhibit the action of T cells as functional regulators and effectors of the immune system.

The present invention also encompasses compositions made with compounds described herein useful for the treatment of immunologically-related diseases and disorders and methods utilizing such compositions for treating such disorders.

DETAILED DESCRIPTION OF THE INVENTION

As used herein, $(C_1-C_4)$alkyl has its conventionally-understood meaning and particularly means linear or branched hydrocarbon chains having from one to four carbon atoms and thus includes methyl, ethyl, propyl, isopropyl, n-butyl, sec-butyl, isobutyl, tert-butyl, and the like.

As used herein, halo$(C_1-C_4)$alkyl has its conventionally-understood meaning and particularly means $(C_1-C_4)$alkyl as used herein wherein hydrogen atoms have been replaced by halogen atoms and thus includes monochloromethyl, trifluoromethyl, difluoroethyl, trifluoropropyl, perfluoro $(C_1-C_4)$alkyl, and the like.

As used herein, perfluoro$(C_1-C_4)$alkyl has its conventionally-understood meaning and particularly means $(C_1-C_4)$alkyl as used herein wherein each hydrogen atom has been replaced by a fluorine atom and thus includes trifluoromethyl.

As used herein, $(CH_2)_n$ has its conventionally-understood meaning and particularly means linear hydrocarbon chains having from one to n carbon atoms and thus includes methylene, ethylene, propylene, n-butylene groups, and the like.

As used herein, the terms halogen, halo, or halide have their conventionally-understood meanings and particularly mean chlorine, bromine, iodine or fluorine.

As used herein, the term "from the range 1 to 6" or the like, means any integral value in the stated range, in this example 1, 2, 3, 4, 5 or 6.

Definitions of terms:

DMF, N,N-dimethylformamide; THF, tetrahydrofuran; TLC, thin-layer chromatography; NMR, nuclear magnetic resonance; TFA, trifluoroacetic acid; HPLC, high performance liquid chromatography; DMAP, 4-dimethylaminopyridine; DMSO, dimethylsulfoxide; $IC_{50}$, concentration giving 50% inhibition; $CC_{50}$, concentration giving 50% cytotoxicity; ND, not determined.

HPLC method used: Analytical HPLC using an HP 1100 HPLC, with a $C_{18}$ Dynamax column (5 cm×4.6 mm, 3 μM particle size, 100 Å pore size), flow rate of 0.5 mL/min, 20%–60% $CH_3CN$ in $H_2O$ over 7.5 min, holding at 60% $CH_3CN$ for 2.5 min, while monitoring at 254 and 210 nm.

EXAMPLES

Example 1

[1,2]-Naphthoquinone was Purchased from Acros Organics and Used as Received.

Examples 2 to 4

The compounds of examples 2 to 4 were prepared substantially in accordance with the procedures disclosed in Takuwa, A.; Soga, O.; Iwamoto, H.; Maruyama, K. *Bull. Chem. Soc. Jpn.* 1986, 59, 2959–2961, which procedures are incorporated herein by reference. The physical properties of the compounds are disclosed in the reference.

Example 2

4-Ethoxy-[1,2]naphthoquinone

Example 3

4-Methoxy-[1,2]naphthoquinone

Example 4

4-Allyloxy-[1,2]naphthoquinone

Examples 5 and 6

The compounds of examples 5 and 6 were prepared substantially in accordance with the procedures disclosed in Perumal, P. T.; Bhatt, M. V. *Synthesis* 1980, 943–945, which procedures are incorporated herein by reference. The physical properties of the compounds are disclosed in the reference.

Example 5

4–Chloro-[1,2]naphthoquinone

Example 6

4-Bromo-[1,2]naphthoquinone

Examples 7 and 8

The compounds of examples 7 and 8 were prepared substantially in accordance with the procedures disclosed in Henrion, J.-C.; Jacquet, B.; Hocquaux, M.; Barre, G.; Hedayatullah, M.; Lion, C. *Bull. Soc. Chim. Belg.* 1996, 105, 415–418. which procedures are incorporated herein by reference. The physical properties of the compounds are disclosed in the reference.

Example 7

4-(1-Methyl-1H-indol-3-yl)-[1,2]naphthoquinone

Example 8

4-(2-Phenyl-1H-indol-3-yl)-[1,2]naphthoquinone

Example 9

4-(2–Chloro-phenyl)-[1,2]naphthoquinone

To a solution of 4-bromo-[1,2]naphthoquinone (350 mg, 1.48 mmol) in THF (20 mL) and $H_2O$ (5 mL) was added 2-chlorophenylboronic acid (231 mg. 1.48 mmol). followed by tri-o-tolylphosphine (45 mg, 148 μmol) and $K_2CO_3$ (614 mg, 4.44 mmol). The mixture was deoxygenated with bubbling $N_2$ for about ten minutes, at which time the $N_3$ line was removed and tris(dibenzylideneacetone)dipalladium(0) (68 mg, 74 μmol) was added. The resultant mixture was heated to reflux for 2 hours under $N_2$, at which point no starting bromide was detectable by TLC (hexanes:ethyl acetate, 1:1, v/v). The mixture was cooled to room temperature and the THF evaporated under reduced pressure. The dried material was dissolved in ethyl acetate, washed sequentially with saturated aqueous ammonium chloride, $H_2O$ and brine, dried over $Na_2SO_4$, filtered, and evaporated under reduced pressure. The isolated material was chromatographed on silica gel (hexanes-ethyl acetate, 4:1, v/v) and dried to yield the product, 4-(2-chloro-phenyl)-[1,2]naphthoquinone, as an orange solid. $^1$H NMR (300 MHz, $CDCl_3$) δ 8.21 (1H, dd, J=6.9, 2.1 Hz), 7.56–7.52 (3H, m), 7.48–7.44(2H, m), 7.44 (1H, m), 6.91 (1H, dd, J=2, 6 Hz), 6.39 (1H, s); HPLC: 7.45 min.

Compounds of examples 10 to 14 inclusive were made by the method of Example 9, by utilizing the appropriate boronic acid.

Example 10

4-(4-Bromo-phenyl)-[1,2]naphthoquinone

Orange solid; $^1$H NMR (300 MHz, $CDCl_3$) δ 8.22 (1H, dd, J=1.8, 7.2 Hz), 7.67 (2H, d, J=6.6 Hz), 7.63–7.60 (2H, m), 7.33 (2H, d, J=6.6 Hz), 7.25 (1H, dd. J=2, 8 Hz), 6.41 (1H, s); HPLC: 8.25 min.

Example 11

4-Phenyl-[1,2]naphthoquinone

Orange-red solid; $^1$H NMR (300 MHz, $CDCl_3$) δ 8.22 (1H, dd, J=1.8, 7.2 Hz), 7.62–7.52(5H, m), 7.46–7.44(2H, m), 7.30(1H, dd, J=1.2, 7.5 Hz), 6.43 (1H, s); HPLC: 6.90 min Example 12

[1,1']Binaphthalenyl-3,4-dione

Orange solid; $^1$H NMR (300 MHz, $CDCl_3$) δ 8.40 (1H, dd, J=1.5, 7.5 Hz), 8.00 (1H, d, J 8.1 Hz), 7.96(1H d, J=8.1 Hz), 7.72(1H, d, J=8.4 Hz), 7.62 (1H, d, J=7.2 Hz), 7.57 (1H, d, J=7.8 Hz), 7.53–7.42 (4H, m), 6.83 (1H, d, J=8.3 Hz), 6.55 (1H, s); HPLC: 8.27 min.

Example 13

4-(3,5-Dichloro-phenyl)-[1,2]naphthoquinone

Orange solid; $^1$H NMR (300 MHz. CDCl$_3$) δ 8.23 (1H, dd, J=1.8, 7.2 Hz), 7.67–7.56 (2H, m), 7.53 (1H, m), 7.41 (1H, m), 7.33 (1H, m), 7.20(1H, d, J=7.5 Hz), 6.40 (1H, s); HPLC: 9.0 min.

Example 14

4-(3-Nitro-phenyl)-[1,2]naphthoquinone

Orange solid; $^1$H NMR (300 MHz, CDCl$_3$) δ 8.41 (1H, d, J=7.2 Hz), 8.34 (1H, s), 8.27 (1H, m), 7.78 (2H, m), 7.63 (2H, m), 7.15 (1H, d, J=7.7 Hz), 6.46 (1H, s); HPLC: 5.78 min.

Examples 15 to 17

The compounds of examples 15 to 17 were prepared substantially in accordance with the procedures disclosed in Barton, D. H. R.; Brewster, A. G. Ley, S. V.; Read, C. M.; Rosenfeld, M. N. *J. Chem. Soc. Perkin Trans. I* 1981, 1473–1476, which procedures are incorporated herein by reference.

Example 15

6-Benzoyl-[1,2]naphthoquinone

Orange solid; $^1$H NMR (300 MHz, CDCl$_3$) δ 8.23 (1H, d, J=7.8 Hz), 7.86 (1H, dd, J=1.5, 7.8 Hz), 7.83–7.79 (3H, m), 7.67 (1H, m), 7.57–7.51 (3H, m), 6.54 (1H, d, J=10.2 Hz); HPLC: 5.93 min.

Example 16

5,6-Dioxo-5,6-dihydro-naphthalene-1–Carboxylic acid methyl ester

This compound was prepared using 5–Carbomethoxy,-2-naphthol as a starting material. The starting material was prepared according to the method of Anderson, L. C.; Thomas, D. G. *J. Am. Chem. Soc.* 1943, 65, 234–238. Orange solid; $^1$H NMR (300 MHz, CDCl$_3$) δ 8.62 (1H, d, J=11 Hz), 8.29 (1H, d, J=7.8 Hz), 8.20 (1H, d, J=7.8 Hz), 7.58 (1H, t, J=7.8 Hz), 6.56 (1H, d, J=11 Hz), 3.99 (3H, s); HPLC: 3.69 min.

Example 17

5,6-Dioxo-5,6-dihydro-naphthalene-2–Carboxylic acid methyl ester

This compound was prepared using 6-carbomethoxy-2-naphthol as a starting material. The starting material was prepared according to the method of Anderson, L. C.; Thomas, D. G. *J. Am. Chem. Soc.* 1943, 65, 234–238. Orange solid; $^1$H NMR (300 MHz, CDCl$_3$) δ 8.17 (2H, m), 8.05 (1H, s), 7.52 (1H, d, J=10.2 Hz), 6.53 (1H, d, J=10.2 Hz), 3.99 (3H, s); HPLC: 3.61 min.

Example 18

7-Hydroxy-[1,2]naphthoquinone

This compound was prepared substantially in accordance with the procedures disclosed in Teuber, H.-J.; Gotz, N. *Chem. Ber.* 1954, 1236–1251, which procedures are incorporated herein by reference. Red solid; $^1$H NMR (300 MHz, DMSO-d$_6$) δ 10.50 (1H, broad s), 7.56 (1H, d, J=9.8 Hz), 7.40 (1H, d, J=8.1 Hz, 7.31 (1H, d, J=2.7 Hz), 7.05 (1H, dd, J=8.1, 2.7 Hz), 6.16 (1H, d, J=9.9 Hz); Anal. Calcd. For C$_{10}$H$_6$O$_3$–0.1H$_2$O: C, 68.26; H, 3.55. Found: C 67.96, 67.89; H, 3.64, 3.65.

Assays for Biological Activity

Method A:

Phosphatase Assay Using pNPP as Substrate:

CD45 enzyme was obtained from BIOMOL (Plymouth Meeting, Pa.). Phosphatase activity was assayed in a buffer containing final concentrations of 25 mM imidazole at pH 7.0, 50 mM NaCl, 2.5 mM ethylenediaminetetraacetic acid ("EDTA"), 5 mM dithiothreitol ("DTT") and 10 μg/mL bovine serum albumin ("BSA") using pNPP as a substrate. Compounds were tested in a range from 30 to 0.01 μM, with a final concentration of 1 or 5% dimethylsulfoxide ("DMSO"), depending on the compound solubility. Activity was measured by following the increase in absorbance at 405 nm using a SpectraMax Plus spectrophotometric plate reader (Molecular Devices, Sunnyvale, Calif.).

Method B:

Cytotoxicity Assay:

Calcein-AM (Molecular Probes, Eugene, Oreg.) uptake, as a quantitative measure of cell viability, was used to evaluate the toxic effect of compounds on T cells. Briefly, PBMC were treated for 3–7 days with 3–10 μg/ml PHA, a potent T-cell mitogen, to preferentially expand the T-cell population. (Bradley, Linda M. *Cell Poliferation in Selected Methods in Cellular Immunology*. Eds. Mishell B. B. and Shiigi. S. M., W. H. Freeman and Co. San Francisco, 1980.)

The T-cell lymphoblasts were purified by separation over Lymphoprep, plated at 2×10$^5$/well in a round bottom 96-well plate containing RPMI with compound and incubated overnight at 37° C. in an incubator containing 5% CO$_2$. The dilution scheme and culture media were the same as those used in the T-cell proliferation assay. After the incubation period. cells were washed with Dulbecco's phosphate-buffered saline (D-PBS) and incubated with 1 μM Calcein-AM for 30–45 min in D-PBS as described in the technical sheet provided with The LIVE/DEAD Viability/Cytotoxicity Kit from Molecular Probes. Percent viability was assessed on a fluorescent plate reader (excitation filter 485/20 nm; emission filter 530/25 nm) where the 100% control value is the fluorescence intensity observed in the absence of test compound.

Method C:

Phosphatase Assay Using lck 10-mer as Substrate:

Phosphatase activity was assayed in 96 well plates in a buffer containing final concentrations of 25 mM HEPES at pH 7.2, 5 mM DTT and 10 μg/mL BSA, using the lck carboxy-terminal peptide TEGQpYQPQP as the substrate (Cho, H., Krishnaraj. R., Itoh. M., Kitas, E., Bannwarth, W., Saito, H., Walsh, C. T. 1993. Substrate specificities of catalytic fragments of protein tyrosine phosphatases (HPTPb, LAR. and CD45) toward the phosphotyrosylpeptide substrates and thiophosphotyrosylated peptides as inhibitors. *Protein Science* 2:977–984). Compounds were tested in a range from 30 to 0.01 μM in a final concentration of 5% DMSO. Enzyme was incubated with substrate. with or without compound, at room temperature for 1.5 h. At the end of the incubation period, BIOMOL "Green Reagent" (BIOMOL, Plymouth Meeting, Pa.) was added to each well, the plates incubated at room temperature for 30 min and absorbance read at 620 nm.

Method D:

Cell Isolation and T Cell Proliferation Assay:

Whole blood was obtained from healthy human blood donors. Peripheral blood mononuclear cells ("PBMC") were isolated using Lymphoprep density-gradient centrifugation (Nycomed Amersham, Oslo, Norway), washed, counted and resuspended at $2 \times 10^6$ cells/mL in RPMI 1640 medium containing glutamine, 0.1 mg/mL gentamycin and 10% heat inactivated human serum. PBMC were transferred to 96-well plates ($2 \times 10^5$ cells/well) containing compound or vehicle control, with the final concentration of DMSO not to exceed 0.3% and incubated for 1 hour before addition of the activating anti-CD3 antibody, OKT3 (30 ng/mL). After 24 hours in culture, the cells were pulsed with [3H]thymidine (1 µCi/well) overnight and harvested the next day onto 96-well Packard GF/C filter plates using a Packard Cell Harvester (Packard Instruments, Meriden, Conn.). The filter plate was dried, the bottom of the plate sealed, 25 µL of Microscint 20 scintillation fluid added to each well, the top of the plate sealed with TopSeal-A, and the plate counted on a Packard TopCount. The data from the TopCount is transferred into Excel 5 (Microsoft, Redmond, Wash.) and formatted for $EC_{50}$ determination using Prism software (GraphPad Software, San Diego, Calif.).

Table 1 shows the inhibition of CD45 activity in the pNPP asssay and the lck assay certain compounds of the present invention. Inhibition in the T cell proliferation assay, as well as results from T cell cytotoxicity assay are shown.

TABLE 1

| Example No. | pNPP $IC_{50}$ (µM) | lck $IC_{50}$ (µM) | T cell prolif. $IC_{50}$ (µM) | $CC_{50}$ (µM) |
|---|---|---|---|---|
| 1 | 3 | >30 | 7 | >30 |
| 2 | 2 | ND | >30 | 30 |
| 3 | 1.2 | 4.2 | >30 | ND |
| 4 | 1.2 | 4.9 | >30 | >30 |
| 5 | 10 | >30 | >30 | >30 |
| 6 | 8.7 | >30 | 22 | >30 |
| 7 | 5 | 19 | 1.5 | >30 |
| 8 | 2.9 | 20 | 2 | 16 |
| 9 | 8 | >30 | 0.3 | 124 |
| 10 | 7.7 | >30 | 0.11 | 3 |
| 11 | 5 | >30 | 0.15 | 12 |
| 12 | 22.5 | >30 | 3.2 | >30 |
| 13 | 5.5 | ND | 0.3 | 5.5 |
| 14 | 7.9 | >30 | 0.2 | 4 |
| 15 | 22 | >30 | 11 | >30 |
| 16 | 11 | >30 | 3.5 | >30 |
| 17 | 7 | >30 | 7 | >30 |
| 18 | 4.9 | ND | >30 | >30 |

What is claimed is:

1. A method for treating autoimmune disorders and organ graft rejection comprising administering to a subject suffering therefrom an effective amount of a compound in accord with structural diagram I:

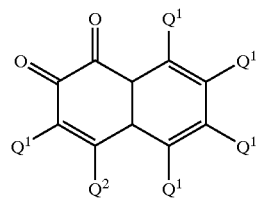

or tautomers thereof or pharmaceutically-acceptable salts thereof, wherein:

$Q^2$ is selected from O-methyl, O-ethyl, O—$CH_2CH=CH_2$, 3-(N-methyl-indole), 3-(2-phenyl-indole), 1-naphthyl, phenyl, 2-chlorophenyl, 4-bromophenyl, 3,5-dichlorophenyl and 3-nitrophenyl, and $Q^1$ is hydrogen.

2. A compound selected from:
   4-(4-bromo-phenyl)-[1,2]naphthoquinone;
   4-(3-nitro-phenyl)-[1,2]naphthoquinone;
   5,6-dioxo-5,6-dihydro-naphthalene-1-carboxylic acid methyl ester, or
   5,6-dioxo-5,6-dihydro-naphthalene-2-carboxylic acid methyl ester.

3. A method for treating immunologically-related diseases, autoimmune disorders and organ graft rejection comprising administering to a subject suffering therefrom an effective amount of a compound selected from:
   4-(4-bromo-phenyl)-[1,2]naphthoquinone;
   4-(3,5-dichloro-phenyl)-[1,2]naphthoquinone;
   4-(3-nitro-phenyl)-[1,2]naphthoquinone;
   5,6-dioxo-5,6-dihydro-naphthalene-1-carboxylic acid methyl ester, or
   5,6-dioxo-5,6-dihydro-naphthalene-2-carboxylic acid methyl ester.

* * * * *